United States Patent
Adkins et al.

[11] Patent Number: 5,723,670
[45] Date of Patent: Mar. 3, 1998

[54] LIQUID AMINES

[75] Inventors: Rick L. Adkins, New Martinsville; William E. Slack, Moundsville, both of W. Va.

[73] Assignee: Bayer Corporation, Pittsburgh, Pa.

[21] Appl. No.: 665,751

[22] Filed: Jun. 18, 1996

[51] Int. Cl.$^6$ .................................................. C07C 209/10

[52] U.S. Cl. .......................... 564/404; 564/399; 564/405; 564/408

[58] Field of Search .................. 564/404, 399, 564/405, 408

[56] References Cited

PUBLICATIONS

CA113:58854, 1989.
CA117:170958, 1991.
Aldrich Chemical Company Catalog, p. 822, 1992.

*Primary Examiner*—Brian M. Burn
*Attorney, Agent, or Firm*—Joseph C. Gil; Lyndanne M. Whalen

[57] ABSTRACT

Amines which are solid at ambient temperature and pressure are liquified by reacting those amines with a derivatizing agent represented by the formula XY in which X represents a halide or sulfonate group and Y represents an alkyl group, a cycloalkyl group, an alkoxyalkyl group or an aryl group. The amine and derivatizing agent are reacted at temperatures of from about 50° to about 250° C. in amounts such that the molar ratio of derivatizing agent to amine groups is from about 0.25:1 to 8:1.

5 Claims, No Drawings

LIQUID AMINES

BACKGROUND OF THE INVENTION

The present invention relates to a process for liquefying amines which are normally solid at ambient temperature and pressure and to the amines produced by that process.

Aromatic amines are known to be useful for many applications. Many of these aromatic amines are, however, solid at ambient temperatures and pressures. It is therefore necessary to form solutions of these amines before using them in processes conducted at low temperatures or to elevate the temperature at which the amine is used in a reaction.

The use of solvents and/or elevated temperatures increases the cost of processes in which these normally solid amines are reacted. The environmental and safety problems presented by using some solvents are also known.

It would therefore be advantageous to be able to use normally solid amines in processes without the need to use a solvent or preliminarily heating the amine to a temperature above the melting point of that amine.

SUMMARY OF THE INVENTION

It is an object of the present invention to provide a process for liquefying an amine which is solid at ambient temperature and pressure without using a solvent or elevating the temperature of the amine prior to use.

It is also an object of the present invention to provide aromatic amines which are liquid at ambient temperature and pressure.

These and other objects which will be apparent to those skilled in the art are accomplished by reacting an aromatic amine represented by the formula $R^3R^2R^1C_6H_2NH_2$ which is normally solid at ambient temperature and pressure with a derivatizing agent represented by the formula X—Y to form a liquid amine in amounts such that the molar ratio of derivatizing agent to amine groups is from about 0.25:1 to about 8:1.

DETAILED DESCRIPTION OF THE INVENTION

The present invention relates to a process for the production of liquid amines based upon aromatic amines which are normally solid at ambient temperature and pressure and to the liquid amines produced by this process.

In the process of the present invention, an aromatic amine represented by the formula $$R^3R^2R^1C_6H_2NH_2 \qquad (I)$$

in which $R^1$ and $R^2$ represents hydrogen, an alkyl group having from 1 to 10 carbons, alkoxy groups, or halides, $R^3$ represents $NH_2$ group, aminophenyl, an alkyl substituted aminophenyl, methylene aniline, an alkyl substituted methylene aniline having from 1 to 10 carbon atoms (e.g., methylene toluidine), a halogen substituted methylene aniline (e.g., methylene-3-chloroaniline), oxyaniline, an alkyl substituted oxyaniline having from 1 to 10 carbon atoms, a halogen substituted oxyaniline.

is reacted with a derivatizing agent represented by the formula

$$X—Y \qquad (II)$$

in which

X represents a halide group or a sulfonate group, and

Y represents an alkyl group having from 1 to 16 carbon atoms, a cycloalkyl group having from 3 to 12 carbon atoms, an alkoxyalkyl group having from 2 to 52 carbon atoms, or an aryl group having from 7 to 12 carbon atoms in amounts such that the molar ratio of derivatizing agent to amine groups is from about 0.25:1 to about 8:1, preferably from about 0.3:1 to about 3:1, most preferably from about 1:1 to about 1.5:1.

Amines corresponding to Formula I in which $R^1$ and $R^2$ represents hydrogen, a methyl group, or a chloride group, $R^3$ represents an $NH_2$ group, a methylene aniline, are preferred amines.

Derivatizing agents represented by Formula II in which

X represents a chloride, bromide, iodide, methyl sulfonate or p-tolyl sulfonate group, and Y represents a benzyl group, an alkyl group having from 4 to 8 carbon atoms, an alkoxy group, are preferred derivatizing agents.

Aromatic amines within the scope of Formula I are known. Specific examples of suitable amines include: o-toluene diamine, m-toluene diamine, 1,2-phenylene diamine, 4,4'-methylene dianiline, oxydianiline, diaminobiphenyls, and substituted diaminobiphenyls.

Preferred aromatic amines include: o-toluene diamine, o-phenylenediamine, and 4,4'-methylene dianiline.

Derivatizing agents within the scope of Formula II are also known. Specific examples of suitable derivatizing agents include: benzyl chloride, cyclohexyl bromide, 2-(2-butoxyethoxy)ethyl mesylate, 2-butyl mesylate, 2-octyl mesylate, 1-butyl mesylate, 1-octyl mesylate, and 2-butyl tosylate.

Preferred derivatizing agents include: benzyl chloride, 2-butyl mesylate, 2-octyl mesylate, and 2-(2-butoxyethoxy) ethyl mesylate.

The process of the present invention is generally carried out at temperatures of from about 50 to about 250° C., preferably from about 80 to about 150° C., most preferably from about 100 to about 125° C.

The process of the present invention may be carried out with a catalyst. Suitable catalysts include alkali metal bases such as sodium hydroxide and potassium carbonate and tertiary amines (aliphatic and aromatic). When used, the catalyst is included in an amount of from about 0.5 to about 1.5 mol of catalyst per equivalent of amine groups.

The process of the present invention may also be carried out using a solvent. Suitable solvents include: toluene, dimethyl formamide, 2-methyl pyrrolidinone, dimethyl sulfoxide, and ethers. When used, it is preferred that the solvent be removed from the product amine prior to using that amine in further reaction processes.

The amines produced by the process of the present invention are liquid and generally have a relatively low viscosity, i.e., a viscosity less than 5,000 mPa.s, preferably less than 3,000 mPa.s, and most preferably less than 1,000 mPa.s. These amines may be used in any of the reaction processes in which the amine of Formula I from which they were derived could be used. For example, the liquid amines of the present invention may be used to produce polyurea elastomers.

Having thus described our invention, the following Examples are given as being illustrative thereof.

EXAMPLES

Example 1

0.82 mol of o-toluene diamine (o-TDA) were added to a 1 liter three-necked flask and heated to 60° C. to melt the o-TDA. 0.82 mol of benzyl chloride were added dropwise to the flask while the contents of the flask were maintained at a temperature below 80° C. Upon completion of the addition of benzyl chloride, the contents of the flask were heated to 100° C. for 1 hour. The contents of the flask were then cooled. 400 ml of toluene and 0.82 mol of sodium hydroxide were added with vigorous stirring. The toluene was vacuum stripped from the reaction mixture and the remaining reaction mixture was filtered.

N,N'-dibenzyl-o-toluenediamine was obtained as a dark liquid having a viscosity of 2825 mPa.s. The composition of the product was confirmed by GC (gas chromatographic) and mass spectrophotometry.

Example 2

0.16 mol of o-TDA, 0.32 mol of cyclohexyl bromide, and 0.33 mol of sodium hydroxide were added to a 250 ml three-necked flask and heated to 150°–160° C. for 6 hours. The solution was then cooled and 100 ml of water were added to the reaction mixture. The resultant mixture was extracted twice with 50 ml of methylene chloride per extraction, dried over anhydrous sodium sulfate and filtered. Water was removed by vacuum stripping.

N,N'-dicyclohexyl-o-toluene diamine was obtained as a dark liquid having a viscosity of 585 mPa.s. The composition of the product was confirmed by GC and mass spectrophotometry.

Example 3

5.73 mol of o-TDA and 12.61 mol of 2-butyl mesylate were added to a 5 liter flask and stirred until the contents were homogeneous. 12.61 mol of sodium hydroxide were added to the flask and the contents of the flask were heated to 100° C. for 2 hours. The contents of the flask were then cooled and 1 liter of water was added with stirring. The layers which formed were separated and the organic layer was dried over anhydrous sodium sulfate. The organic layer was then filtered and vacuum stripped.

N,N'-di-(2(2-butyl)-o-toluene diamine was obtained as a dark liquid having a viscosity of 27 mPa.s. The composition of the product was confirmed by GC and mass spectrophotometry.

Example 4

Example 3 was repeated using m-toluene diamine instead of o-TDA. N,N'-di-(2-butyl)-m-toluene diamine was recovered as a dark liquid having a viscosity of 50 mPa.s. The composition of the product was confirmed by GC and mass spectrophotometry.

Example 5

0.062 mol of o-TDA, 0.125 mol of 2-(2-butoxyethoxy) ethyl mesylate and 0.062 mol of potassium carbonate were added to a 250 ml three-necked flask. The contents of the flask were heated to 100° C. for 4 hours. The contents of the flask were then cooled. 100 ml of methylene chloride and 80 ml of water were added to the flask with stirring. The layers which formed were separated and the organic layer dried over anhydrous sodium sulfate and filtered. Water was vacuum stripped from the organic layer.

N,N'-di-(2-(2-butoxyethoxy)ethyl)-o-toluene diamine was recovered as a dark liquid having a viscosity of 28 mPa.s. The composition of the product was confirmed by GC and mass spectrophotometry.

Example 6

0.46 tool of 1,2-phenylene diamine, 0.92 mol of 2-butyl mesylate and 0.92 tool of sodium hydroxide were added to a 500 ml three-necked flask. The contents of the flask were heated to and maintained at 100° C. for 3 hours. The contents of the flask were then cooled and 80 ml of water were added to the flask with vigorous stirring for 20 minutes. The water was vacuum stripped and the remaining solution was filtered.

N,N'-di-(2-butyl)-o-phenylene diamine was recovered as a dark liquid having a viscosity of 20 mPa.s. The composition of the product was confirmed by GC and mass spectrophotometry.

Example 7

0.050 mol of 4,4'-methylene dianiline and 0.151 mol of 2-butyl mesylate were added to 250 ml three-necked flask and heated at 100° C. for 2.5 hours. The contents of the flask were then cooled and 0.151 mol of sodium hydroxide, 100 ml of water and 100 ml of methylene chloride were added. After 10 minutes of vigorous stirring, the phases which formed were separated. The organic phase dried over anhydrous sodium sulfate, filtered and vacuum stripped.

N,N'-di-(2-butyl)-4,4'-methylene dianiline was recovered as a clear red liquid having a viscosity of 1130 mPa.s. The composition of the product was confirmed by GC and mass spectrophotometry.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a liquid aromatic amine comprising reacting 1) an amine represented by the formula $R^3R^2R^1C_6H_2NH_2$ in which $R^1$ and $R^2$ each represents hydrogen, an alkyl group having from 1 to 10 carbon, alkoxy groups, or halides, and $R^3$ represents an $NH_2$ group, aminophenyl, an alkyl substituted aminophenyl, methylene aniline, an alkyl substituted methylene aniline having from 1 to 10 carbon atoms, a halogen substituted methylene aniline, oxyaniline, an alkyl substituted oxyaniline having from 1 to 10 carbon atoms, a halogen substituted oxyaniline.

which amine is normally solid at ambient temperature and pressure with a derivatizing agent represented by the formula

X—Y in which

X represents a halide group or a sulfonate group, and

Y represents an alkyl group having from 1 to 16 carbon atoms, a cycloalkyl group having from 3 to 12 carbon atoms, an alkoxyalkyl group having from 2 to 52 carbon atoms, an aryl group having from 7 to 12 carbon atoms, in amounts such that the molar ratio of derivatizing agent 2) to amine groups in 1) is from about 0.25:1 to about 8:1.

2. The process of claim 1 in which amine 1) is o-toluene diamine, m-toluene diamine, 1,2-phenylene diamine, 4,4'-methylene dianiline, a diaminobiphenyl or an alkyl-substituted diaminobiphenyl.

3. The process of claim 1 in which derivatizing agent 2) is benzyl chloride, cyclohexyl bromide, 2-(2-butoxyethoxy)ethyl mesylate, 2-butyl mesylate or 2-octyl mesylate.

4. The process of claim 1 in which the reaction is carried out at a temperature of from about 50° to about 250° C.

5. The liquid amine produced by the process of claim 1.

* * * * *